United States Patent [19]

Valenti et al.

[11] Patent Number: 5,834,424
[45] Date of Patent: Nov. 10, 1998

[54] **USE OF LACTOFERRIN FOR THERAPY OF ACUTE OF CHRONIC INFECTIOUS DISEASES BY THE INTRACELLULAR GRAM-POSITIVE PATHOGENS *STREPTOCOCCUS PYOGENES* AND *STAPHYLOCOCCUS AUREUS***

[75] Inventors: Piera Valenti, Rome; Giovanni Antonini, Caprarola, both of Italy

[73] Assignee: Gambit International Limited, Tortola, Virgin Islands (Br.)

[21] Appl. No.: 924,093

[22] Filed: Sep. 5, 1997

Related U.S. Application Data

[63] Continuation-in-part of Ser. No. 677,594, Jul. 9, 1996, abandoned.

[30] Foreign Application Priority Data

Jul. 12, 1995 [IT] Italy ................................. RM95A0473

[51] Int. Cl.⁶ ........................... A61K 37/02; A61K 31/43; A61K 31/545; C07K 13/00
[52] U.S. Cl. ........................ 514/8; 514/2; 514/6; 514/12; 514/21; 514/192; 514/200; 530/324; 530/400; 530/832; 530/873; 424/439; 424/442; 424/532; 424/657; 426/332; 426/334; 426/335; 426/442
[58] Field of Search .................. 514/6, 8, 12, 2, 514/21, 192, 200; 530/324, 400, 832, 873; 424/439, 442, 532, 657; 426/332, 334, 335, 442

[56] References Cited

U.S. PATENT DOCUMENTS 5,198,419 3/1993 Ando et al. .................................. 514/8
5,296,464 3/1994 Tomita et al. .............................. 514/6
5,656,951 8/1997 Tomita et al. .............................. 514/6

FOREIGN PATENT DOCUMENTS 431933 12/1990 European Pat. Off. .
438750 12/1990 European Pat. Off. .
629347 11/1992 European Pat. Off. .
568200  4/1993 European Pat. Off. .
9413318 12/1993 WIPO .

OTHER PUBLICATIONS

Bacterial Activity of Union Lactoferrin:Sensitivity of a Variety of Microorganisms Infect Immun 28:893–898 (1980).

Antiviral Effects of Plasma and Milk Proteins . . . JID vol. 172, pp. 380–387 (Aug. 1995).

Lactoferrin INhibits Herpes Simples Virus . . . (Marchetti, Magda) (1996).

Antiviral Effects of Milks Proteins . . . Aids Research and Human Retrovirus (Swart, P.L.) (1996).

*Primary Examiner*—Cecilia J. Tsang
*Assistant Examiner*—Jennifer Harle
*Attorney, Agent, or Firm*—Guido Modiano; Daniel J. O'Byrne

[57] ABSTRACT

Compositions of lactoferrin, ovotransferrin or serotransferrin in apo or iron-saturated form are provided which have bacterial anti-invasive properties against *Streptococcus pyogenes* and *Staphylococcus aureus*. Methods of treatment of epithelial calls and mucosal membranes are described.

12 Claims, No Drawings

USE OF LACTOFERRIN FOR THERAPY OF ACUTE OF CHRONIC INFECTIOUS DISEASES BY THE INTRACELLULAR GRAM-POSITIVE PATHOGENS *STREPTOCOCCUS PYOGENES* AND *STAPHYLOCOCCUS AUREUS*

This application is a continuation-in-part application Ser. No. 08/677,594 filed on 09 Jul. 1996, abandoned.

BRIEF DESCRIPTION OF THE INVENTION

The present invention demonstrates a protective effect of lactoferrin in apo and iron-saturated forms inhibiting the entry into the host cells of intracellular Gram positive pathogen bacteria, like *Streptococcus pyogenes* and *Staphylococcus aureus*. This new function, defined as anti-invasive activity is not related to the well known antibacterial activity of lactoferrin and to the other known properties of the protein. The same anti-invasive activity of lactoferrin is also exerted, but to a lesser extent, by other transferrins: ovotransferrin and serotransferrin.

TECHNICAL FIELD

The present invention relates to the therapeutic utilization of lactoferrin for curing acute and preventing chronic (and recurrent) bacterial infectious diseases of humans, caused by intracellular Gram positive pathogen bacteria.

BACKGROUND ART

It has been demonstrated that, at the beginning of a bacterial infection, there could be an initial phase of adhesion to host cells. Some pathogen bacteria are only able to adhere to the cells through specific surface structures, whereas others are able to penetrate inside the cell, to remain viable in the phagosome or to replicate in the cytoplasm escaping from the vacuole.

The bacterial structures promoting the internalization are virulence factors because the intracellular localization of bacteria allow them to avoid the action of the immune system and the pharmacological therapy.

The facultative intracellular bacteria can multiply inside the host cell, causing an acute infection, or can survive into the cell in a resting state causing continuous recurrences when the bacterial multiplication starts again.

The presence of intracellular bacteria surviving in a resting state can explain the recurrence of bacterial infections of ephitelium and mucosas, such as the recurrent infections of oropharyngeal mucosa by *Streptococcus pyogenes*. Beta-hemolytic Streptococci are the etiological agents of several diseases in humans such as erysipelas, puerperal fever, sepsis, streptococcal angina, impetigo, endocarditis, genital-urinary infections, rheumatic fever and glomerulonephritis. In particular, streptococcal angina is a recurrent infection very common in children caused by Group A-Streptococci. Their pathogenic power is exerted by adhering to cells of pharyngeal epithelium with the aim of specific structures (lypoteicoic acids and M substance) and producing rhinopharyngitis, tonsillitis, mucous edema, swelling and ache of cervical lymphonodes. It has been widely demonstrated that, in spite of an antibiotic treatment (usually penicillin or erythromycin), it is possible to observe in most patients the recurrence of these infections. As a matter of fact, after stopping the efficacious antibiotic therapy, owing to the patient's apparently full clinical recovery (this occurrence can be also supported by a microbiological control showing the absence of such a microorganism in viable form in pharyngeal isolates), the infection often reappears within 2–4 weeks.

Such recurrent behavior of the streptococcal infection can be ascribed to a recently demonstrated invasive capability of *S. pyogenes* that, by adhering and penetrating inside epithelial cells, eludes both the immune system and the antibiotic treatment. The invasive capability of *Staphylococcus aureus* towards epithelial cells has also been recently demonstrated. In particular, this pathogen bacterium colonizes human epithelium and causes suppurative infectious diseases. Beside epithelium infections, *S. aureus* causes serious deep infections such as abscesses in organs, osteomyelitis, pyelonephritis, pneumonia, empyema, purulent arthritis, septicemia and endocarditis. Also in these infections, the usual pharmacological therapy is based on the antibacterial activity of the administered substances towards microorganisms. It should be stressed that pharmacological therapies inhibiting bacterial penetration inside the cells of the host organism are not so far available. However, from what is above stated, it appears evident that a therapy preventing the adhesion and the entry of *Streptococcus pyogenes* and *Staphylococcus aureus* into epithelial cells will be extremely important as adjuvant in the antibacterial therapy. In fact, the inhibition of the bacterial entry into the cells allows the chemiotherapic substances to eliminate and kill streptococci from the surface of pharyngeal epithelium. Both the inhibition of bacterial entry and killing of extracellular bacteria could significantly reduce the frequency of infections in adults and children. This kind of therapy has hertofore never been used.

The biological activity of substances able to inhibit bacterial entry into host cells is called "anti-invasive activity" in the scientific literature.

The anti-invasive activity exerted by lactoferrin towards *S. pyogenes* and *S. aureus*, facultative intracellular Gram positive bacteria, as described in the present invention, may fill such deficiency thus making possible the use of lactoferrin to cure acute and prevent chronic (and recurrent) infections caused by these bacteria.

DISCLOSURE OF THE INVENTION

The therapeutic model described in the present invention is based on the anti-invasive activity towards bacteria exerted by lactoferrin (and ovotransferrin and serotransferrin), and represents therefore a new approach for the therapy of bacterial infections caused by intracellular Gram positive pathogen bacteria.

Lactoferrin (or ovotransferrin or serotransferrin) having very low or no toxicity can therefore be utilized by topical route in bacterial infections concerning epithelium and mucosas like oropharyngeal, nasal, bronchial, and vaginal.

The object of the present invention is the therapeutic utilization of the anti-invasive activity towards facultative intracellular Gram-positive pathogen bacteria, exerted by lactoferrin, ovotransferrin, and serotransferrin at the concentration to which the well known antibacterial activity of these proteins is absent. All these glycoproteins are highly homologous (about 70%) in their amino acid sequences and all belong to the transferrin protein family.

As an example, the in vitro activity of lactoferrin (or ovotransferrin or serotransferrin) will be shown to protect cultured human epithelial cells (chosen as cells representative of human oropharyngeal or vaginal epithelium) from the invasion of *Streptococcus pyogenes* (chosen as intracellular Gram-positive pathogen bacterium responsible for the pathology correlated to recurrent oropharyngeal infections). The anti-invasive activity, possessed by lactoferrin (or ovotransferrin or serotransferrin), toward invasive bacteria is put in evidence by the about a 100 fold decrease of *S. pyogenes* cells inside cultured human epithelial cells (HeLa or Hep 2 cell lines) occurring when lactoferrin (or ovotransferrin or serotransferrin) is present at the same time as the cells and the microorganism at non-cytotoxic nor bactericidal concentrations (up to 2 mg/ml).

Since there is no animal model commonly considered suitable for testing substances with anti-invasive activity towards *Streptococcus pyogenes*, the examples below-reported have been performed with in vitro models, that are generally used for assaying substances which inhibit the bacterial entry into the host cells.

Furthermore, it is hereby demonstrated that the anti-invasive property of lactoferrin is also exerted towards *Staphylococcus aureus*, another facultative intracellular Gram-positive pathogen bacterium, thus making evident the possibility of a therapeutic utilization of lactoferrin in order to cure acute or to prevent recurrent infections dependent on the internalization of this pathogen into epithelial host cells.

WAYS OF CARRYING OUT THE INVENTION

The term lactoferrin designates a glycoprotein present in milk, in many biological secretions and in the leucocyte granules of mammals. Lactoferrin possesses an isoelectric point of 7.8, a molecular weight of about 83,000 Da, two sugar chains containing the 7–10% of carbohydrates based on the total weight. Lactoferrin is known to bind 2 atoms of $Fe^{3+}$ per molecule. It is known to control the amount of free iron in biological liquids, inhibiting the bacterial growth (the bacteriostatic property of lactoferrin is already well known) and decreasing the risk of forming free radicals due to the presence of non-chelated iron. Lactoferrin, ovotransferrin, and serotransferrin belong to a family of glycoproteins generally called "Transferrins", characterized in that they possess two binding sites for $Fe^{3+}$ per molecule and a high degree of amino acid sequence homology among them (about 70%).

Bovine lactoferrin is industrially produced by extraction from bovine milk. In the experiments described in the present invention, bovine lactoferrin was used, but the same anti-invasive activity described in the present invention is possessed by all the marketable proteins known as lactoferrin such as human lactoferrin or mouse lactoferrin, produced by extraction and purification from biological samples, or by recombinant DNA technique, and, therefore, the anti-invasive activity of lactoferrin has been extended, as described in the present invention, to all the lactoferrins from any source, or produced in any way.

The anti-invasive activity towards the above-stated microorganisms exerted by lactoferrin, the therapeutic utilization of which is an object of the present invention, is also possessed by ovotransferrin and human serotransferrin even if they show a lesser activity.

Furthermore, different $Fe^{3+}$ saturations of the above glycoproteins, from apo-forms to totally $Fe^{3+}$ saturated forms have been utilized. All the preparations of these transferrins, having different $Fe^{3+}$ saturation, showed the same anti-invasive activity.

The therapeutic utilization of the anti-invasive activity towards *Streptococcus pyogenes* and *Staphylococcus aureus*, exerted by lactoferrin, an object of the present invention, has been shown at concentrations of lactoferrin which are not toxic towards the cultured human epithelial cells nor bactericidal towards the tested microorganisms. It is very important to use lactoferrin at concentrations sufficiently low so that its antibacterial activity is not present. The bacterial invasion, contrary to the phagocitosis by professional phagocytes, requires an active metabolism by host cells and bacteria. The substances showing the anti-invasive activity must be, therefore, assayed at non-bactericidal concentrations, because non-viable bacteria are unable to enter within the host cells and, therefore, no inhibition of bacterial invasion can be observed.

Lactoferrin (and ovotransferrin and serotransferrin) has been tested for the anti-invasive activity towards *Streptococcus pyogenes*, utilized as intracellular Gram-positive pathogen bacteria prototype, by means of the inhibition of both the adhesion early phases and bacterial internalization according to the experimental model below described.

Lactoferrin (or ovotransferrin or serotransferrin) has been also tested for the anti-invasive activity towards an other bacterium such as *Staphylococcus aureus* using an analogous protocol.

The utilization of lactoferrin (or ovotransferrin or serotransferrin) in the therapy of streptococcal infections of the oropharynx is therefore only one of the possible therapeutic applications of the lactoferrin anti-invasive activity described in the present invention. In fact, the anti-invasive properties of lactoferrin (or ovotransferrin or serotransferrin) also allow its utilization for the topical therapy of many acute or chronic (or recurrent) infections by these intracellular Gram-positive pathogen bacteria concerning epithelium and mucosas such as oropharyngeal, nasal, bronchial, and vaginal.

The lactoferrin (or ovotransferrin or serotransferrin) activity according to the present invention can be obtained using lactoferrin (or ovotransferrin or serotransferrin) stored in liquid form, as solutions at concentrations of 0.1 to 10% weight/volume (g/ml) of the protein in solvents acceptable for pharmaceutial use, in particular water, or in solid form (lyophilized, dried, or frozen) and in the other commonly known forms of storage; for example, immobilized or adsorbed on an inert support commonly used in the pharmaceutical field.

Lactoferrin (or ovotransferrin or serotransferrin), with respect to the activity according to the invention, can thus be used in the liquid form, as a rinse or gargle, or in solid form, such as granular form to be dissolved in water for preparing a gargle just before using, with the concentrations specified above or also in powder for use on the skin. Alternatively, it is possible to incorporate the protein mixture of the invention in a formulation to be chewed, such as chewing gum, tablets, pastilles, lozenges, etc. in a concentration of 1 to 60% by weight of the total formulation.

In its ready-for-use form, the lactoferrin (or ovotransferrin or serotransferrin) formulation with respect to the activity according to the invention, can also comprise further conventional antibiotic and antibacterial compounds as well as carriers, fillers, flavoring agents, preservatives, surfactants, colorants and other adjuvants selected from those conventionally used for the various liquid or solid form preparations for oral topical use and for skin topical use.

Thus, lactoferrin (or ovotransferrin or serotransferrin) formulation, with respect to the activity according to the invention, can also comprise antibiotic compounds like: penicillins, cephalosporins, chloromphenicol, macrolids, aminoglycosides, sulphamidics, etc. and other anti-bacterial compounds, such as quaternary ammonium compounds with one long chain alkyl on the nitrogen atom, alkali metal pyrophosphates and orthophosphates, halogenated bisphenols and halogenated diphenyl ethers, sodium benzoate, sodium salicylate, etc.

Lactoferrin (or ovotransferrin or serotransferrin) formulation, with respect to the activity according to the invention, can further comprise humectants, e.g. glycerin, sorbitol, xylitol, propylene glycol, atc., flavours, e.g. oil of spearmint, peppermint or cinnamon, menthol, methyl salicylate, atc., sweetening agents, e.g. aspartame, saccharin, dextrose, cyclamate, wintergreen, etc., thickening agents, e.g., xanthan gum, carrageenin, carboxymethyl cellulose, etc.

The formulation to be chewed by the user includes a respective conventional base material and conventional adjuvant such as flavouring, sweetening and coloring agents, humectants, etc., as those mentioned above, and thickening and gelling agents such as thickening silica, natural or synthetic gums, e.g. tragacanth gum, guar gum, hydroxyethyl- and carboxymethyl cellulose, polyvinyl pyrrolidone, starch, etc.

Lactoferrin (or ovotransferrin or serotransferrin) formulations, with respect to the activity according to the invention, in either liquid or solid form, should be used for purposes of prevention of recurrent infectious diseases by S. pyogenes or by S. aureus at least once, preferably twice a day. For purposes of treatment, the frequency of use can be increased up 3 to 4 times a day.

The hereby described examples provide strong evidence that the therapeutical utilization of the anti-invasive activity towards intracellular Gram-positive pathogen microorganisms Streptococcus pyogenes and Staphylococcus aureus possessed by lactoferrin (and ovotransferrin and serotransferrin), an object of the present invention, can be considered optimal as regards the common therapeutical treatments, since it can be utilized alone or as an adjuvant in antibacterial therapies towards acute or chronic (or recurrent) infections by intracellular pathogen bacteria.

EXAMPLES

It must be stated in advance that the real evaluation of the invasive capability of S. pyogenes must occur through a specific experimental procedure that we described below:

Assay of Invasive Activity of Streptococcus pyogenes

Semiconfluent monolayers of HeLa and Hep-2 cells are infected with a bacterial suspension (100 exponentially grown bacteria per cell) corresponding to 120 min subculture at 37° C. After the bacterial infection (2 h at 37° C.) in the presence and absence of lactoferrin (or ovotransferrin or serotransferrin), the monolayer is five-fold washed with phosphate buffered saline (PBS) and then fresh medium (MEM, Seromed) containing 200 ug/ml of gentamycin was added. This antibiotic is well known for its inability to penetrate into the eucaryotic cells exerting its bactericidal effect only towards the extracellular bacteria (free or adhered).

After 2 h incubation period at 37° C. in gentamycin, the infected cells are lysed by the addition of cold Triton-X 100 (0.1%).

The cellular lysate is diluted with PBS and plated on Todd-Hewitt agar in order to quantify the number of viable intracellular bacteria.

TRANSFERRINS: identical results were obtained using human or bovine lactoferrin and, therefore, no distinction between them is reported in the text. Serotransferrin in the text means human lactoferrin. Ovotransferrin in the text means hen's ovotransferrin.

EXAMPLE 1

Anti-invasive Activity of Lactoferrin Towards S. pyogenes at Non-cytotoxic nor Bactericidal Concentrations Initially, the minimal toxic concentration was evaluated towards the cells. Different lactoferrin concentrations were kept in contact with cell monolayers. After 24 h, the monolayers were examined by optical microscopy after vital staining.

TABLE 1

Assay of cytotoxicity of lactoferrin at different concentrations.

| Lactoferrin (mg/ml) | Hep 2 | HeLa cells |
|---|---|---|
| 0 | − | − |
| 0.25 | − | − |
| 0.50 | − | − |
| 1.0 | − | − |
| 2.0 | − | − |
| 4.0 | − | − |
| 8.0 | − | − |
| 50 | + | + |

The cytotoxic effect was evaluated by examining the cell morphology and vitality (−) no cytotoxic effect (+) presence of cytotoxicity The lactoferrin was also tested in order to quantify the minimal concentration not inhibiting bacterial growth.

TABLE 2

Antibacterial activity of lactoferrin.

| Lactoferrin (mg/ml) | S. pyogenes (CFU/ml) | S. aureus (CFU/ml) |
|---|---|---|
| 0 | $2 \times 10^8$ | $6 \times 10^8$ |
| 0.5 | $2 \times 10^5$ | $6 \times 10^8$ |
| 1.0 | $2 \times 10^8$ | $6 \times 10^8$ |
| 2.0 | $2 \times 10^8$ | $6 \times 10^8$ |
| 5.0 | $5 \times 10^7$ | $2 \times 10^8$ |
| 10.0 | $1 \times 10^7$ | $6 \times 10^7$ |

The antibacterial activity of lactoferrin was carried out in complete medium with lactoferrin added and incubated at 37° C. for 18 h. After this period, the colony forming units (CFU) were counted on Todd-Hewitt agar. The inoculum consisted of about $5 \times 10^5$ $^{cell/ml}$.

The anti-invasive effect of lactoferrin at non-cytotoxic nor bactericidal concentrations (1 mg/ml and 2 mg/ml) was tested utilizing one strain of S. pyogenes inoculated in HeLa or Hep 2 cell monolayer.

TABLE 3

Effect of lactoferrin on the invasion ability of S. pyogenes.

| | Internalized bacteria (CFU/ml) | |
|---|---|---|
| Lactoferrin (mg/ml) | Hela cells | Hep 2 cells |
| 0 | $5 \times 10^5$ | $2 \times 10^5$ |
| 1.0 | $5 \times 10^3$ | $1 \times 10^3$ |
| 2.0 | $1 \times 10^3$ | $2 \times 10^2$ |

The anti-invasive effect of lactoferrin was demonstrated by a drastic decrease of the number of internalized bacteria in both cultured cells.

The anti-invasive effect of lactoferrin (1 mg/ml) has been also compared with that obtained utilizing ovotransferrin (1 mg/ml), and serotransferrin (1 mg/ml), at different saturations with $Fe^{3+}$.

The data are shown in Table 4. In this experiment HeLa cell monolayers were used.

TABLE 4

Anti-invasive activity in apo and iron-saturated forms of ovotransferrin and serotransferrin in comparison with lactoferrin towards *S. pyogenes*.

| Protein at 1.0 mg/ml | Internalized bacteria (CFU/ml) |
| --- | --- |
| None | $5 \times 10^5$ |
| Apo lactoferrin | $5 \times 10^3$ |
| Apo ovotransferrin | $1 \times 10^5$ |
| Apo serotransferrin | $1 \times 10^5$ |
| Lactoferrin 50% $Fe^{3+}$ saturated | $3 \times 10^3$ |
| Ovotransferrin 50% $Fe^{3+}$ saturated | $1 \times 10^5$ |
| Serotransferrin 50% $Fe^{3+}$ saturated | $5 \times 10^4$ |
| Lactoferrin 100% $Fe^{3+}$ saturated | $3 \times 10^3$ |
| Ovotransferrin 100% $Fe^{3+}$ saturated | $8 \times 10^4$ |
| Serotransferrin 100% $Fe^{3+}$ saturated | $7 \times 10^4$ |

As demonstrated, the anti-invasive effect of ovotransferrin and serotransferrin, if present, is less than that observed with lactoferrin.

It must be stressed that the above-mentioned anti-invasive activity of lactoferrin, serotransferrin and ovotransferrin is not affected by the degree of iron saturation (50 or 100%) of the above mentioned proteins.

EXAMPLE 2

Anti-invasive Activity of Lactoferrin Towards *S. pyogenes* in Presence of Subinhibiting Concentrations of Antibiotics It is well known that *S. pyogenes* is sensitive to the antibacterial action of erythromycin and ampicillin. Subinhibiting amounts of erythromycin or ampicillin were utilized in order to verify if the bacteria, pretreated with this antibiotic were inhibited in their invasion efficiency. The invasion test was performed as noted above, only utilizing viable bacterial cells and, consequently, the antibiotic must be used at subinhibiting concentrations, since only those subinhibiting concentrations of antibiotics not affecting the microbial viability, allow the bacterial entry inside the cell.

In these experiments, *S. pyogenes* was cultured in the presence of subinhibiting concentrations of antibiotics and the invasivity test was performed with this bacterial inoculum. The data are reported in Table 5.

TABLE 5

Effect of subinhibiting concentrations of antibiotics towards the invasivity of *S. pyogenes* in absence of lactoferrin.

| Antibiotics (μg/ml) | Internalized bacteria (CFU/ml) |
| --- | --- |
| 0 | $5 \times 10^5$ |
| Erythromycin 20 | $2 \times 10^5$ |
| Ampicillin 0.1 | $2 \times 10^5$ |

The data demonstrate that bacteria pretreated with antibiotics do not lose their invasion capability.

The anti-invasive activity of lactoferrin was tested towards *S. pyogenes* pretreated with subinhibiting amounts of erythromycin or ampicillin. The effect of lactoferrin was tested towards *S. pyogenes* grown for 24 h in the presence of erythromycin (20 ug/ml) or in the presence of ampicillin (0.1 ug/ml). The results are shown in Table 6. HeLa cell monolayers were used.

TABLE 6

Anti-invasive activity of transferrins towards *S. pyogenes* pretreated with antibiotics.

| Transferrins | (mg/ml) | Antibiotic (μg/ml) | Intracellular bacteria (CFU/ml) |
| --- | --- | --- | --- |
| None | | 0 | $5 \times 10^5$ |
| Lactoferrin | 1 | 0 | $6 \times 10^3$ |
| Lactoferrin | 2 | 0 | $2 \times 10^3$ |
| Lactoferrin | 1 | Erythromycin 20 | $3 \times 10^1$ |
| Lactoferrin | 2 | Erythromycin 20 | 0 |
| Lactoferrin | 1 | Ampicillin 0.1 | 0 |
| Ovotransferrin | 1 | 0 | $1 \times 10^5$ |
| Ovotransferrin | 2 | 0 | $8 \times 10^4$ |
| Ovotransferrin | 1 | Erythromycin 20 | $6 \times 10^4$ |
| Ovotransferrin | 2 | Erythromycin 20 | $4 \times 10^4$ |
| Ovotransferrin | 1 | Ampicillin 0.1 | $5 \times 10^4$ |
| Serotransferrin | 1 | 0 | $3 \times 10^5$ |
| Serotransferrin | 2 | 0 | $3 \times 10^5$ |
| Serotransferrin | 1 | Erythromycin 20 | $1 \times 10^5$ |
| Serotransferrin | 2 | Erythromycin 20 | $6 \times 10^4$ |
| Serotransferrin | 1 | Ampicillin 0.1 | $6 \times 10^4$ |

The same test was performed with other antibiotics like cephalosporins, vancomycin, bacitracin, cycloserine, phosphomycin and fairly similar results were obtained. It is evident that the anti-invasive activity of lactoferrin increases when bacteria are pretreated with antibiotics, demonstrating the cooperative effect of a therapeutic treatment of lactoferrin and antibiotics against infectious diseases by intracellular pathogen bacteria. Similar results were obtained with iron saturated forms.

EXAMPLE 3

Protective Activity of Lactoferrin Towards the Penetration of *Staphylococcus aureus* Inside the Cell The anti-invasive activity towards the facultative intracellular bacterium *Staphylococcus aureus* was performed by means of the described protocol, only modifying the type of the selective medium (Mannitol salt agar) in which C.F.U. were counted. The test was performed utilizing a HeLa cell monolayer.

TABLE 7

Anti-invasive activity of lactoferrin, serotransferrin and ovotransferrin (at the concentration of 1 mg/ml) and also in presence of subinhibiting amounts of erythromycin (0.02 mg/ml) and ampicillin (0.1 μg/ml) towards intracellular pathogen Gram-positive bacterium *Staphylococcus aureus*.

| Proteins | Intracellular bacteria (CFU/ml) *Staphylococcus aureus* |
| --- | --- |
| Control | $7 \times 10^5$ |
| Erythromycin | $3 \times 10^5$ |
| Ampicillin | $2 \times 10^5$ |
| Lactoferrin | $6 \times 10^3$ |
| Serotransferrin | $4 \times 10^5$ |
| Ovotransferrin | $8 \times 10^4$ |
| Lactoferrin + Erythromycin | 0 |
| Lactoferrin + Ampicillin | 0 |
| Ovotransferrin + Erythromycin | $5 \times 10^4$ |

TABLE 7-continued

Anti-invasive activity of lactoferrin, serotransferrin and ovotransferrin (at the concentration of 1 mg/ml) and also in presence of subinhibiting amounts of erythromycin (0.02 mg/ml) and ampicillin (0.1 μg/ml) towards intracellular pathogen Gram-positive bacterium *Staphylococcus aureus*.

| Proteins | Intracellular bacteria (CFU/ml) *Staphylococcus aureus* |
|---|---|
| Ovotransferrin + Ampicillin | $6 \times 10^4$ |
| Serotransferrin + Erythromycin | $1 \times 10^5$ |
| Serotransferrin + Ampicillin | $2 \times 10^5$ |

From Table 8, it is possible to deduce that the lactoferrin, ovotransferrin and serotransferrin, even if at different degrees are active toward all the examined intracellular Gram-positive pathogen bacteria and that this activity is increased in presence of antibiotic substances utilized at subinhibiting concentrations. Similar results were also obtained with iron saturated forms.

EXAMPLE 4

Gargle

Composition per 100 ml

Active Ingredients

Human lactoferrin, from milk, SIGMA Chemical Co, cat L0520, 1.0 g.

Carriers, Preservatives and Flavouring Agents

Sodium chloride 1 g
Sodium bicarbonate 100 mg
Methyl-p-hydroxybenzoate 100 mg
Peppermint oil 50 mg
Purified water to 100 ml Use For prevention and curing Streptococcical angina two gargles a day, one in the morning, one in the evening.

EXAMPLE 5

Envelope Packs

Composition for 1 envelope

Active Ingredients

Lactoferrin, from bovine milk, SIGMA Chemical Co., cat L4765, 1.0 g.
Erythromycin 0.2 g Carriers, Preservatives and Flavouring Agents Sodium choloride 20 mg
Sodium bicarbonate 10 mg
Methyl-p-hydroxybenzoate 20 mg
Peppermint oil 5 mg Use For preventing and curing Streptococcal angina, the content of an envelope is dissolved in 20 ml water for two rinses, one in the morning and one in the evening.

EXAMPLE 6

Chewing Gum

Composition of one piece of gum

Active Ingredients

Lactoferrin, from bovine milk, SIGMA Chemical Co. cat L4765, 250 mg.
Benzalkonium chloride 10 mg Carriers, Preservatives and Flavoring Agents Gum base (Paloya TX) 400 mg
Glucose 100 mg
Glycerol 10 mg
Sodium bicarbonate 10 mg
Methyl-p-hydroxybenzoate 20 mg
Peppermint oil 5 mg Use For preventing and curing Streptococcical angina, one piece of chewing gum in the morning, one in the evening.

EXAMPLE 7

Powder

Composition for 100 g

Active Ingredients

Lactoferrin from bovine milk, SIGMA Chemical Co., cat L 4765, 10 g
ampicillin 1 g Carriers, Preservatives corn starch 85 g
zin oxide 3 g
thickening silica powder 1 g Use For curing staphylococcal infections of skin apply twice a day.

We claim:

1. A method for inhibiting penetration of Gram positive bacteria selected from the group consisting of *Streptococcus pyogenes, Staphylococcus aureus* and mixtures thereof into host cells by administering a transferrin selected from the group consisting of lactoferrin, ovotransferrin, serotransferrin and mixtures thereof in association with a pharmaceutically acceptable carrier, wherein said transferrin is topically administered at an anti-invasive, non-cytotoxic nor bactericidal concentration.

2. A method according to claim 1, wherein said transferrin is administered in a liquid form at a concentration of up 2% by weight/volume.

3. A method according to claim 1, wherein said transferrin is in the apo or iron-saturated form.

4. A method according to claim 1, wherein said transferrin is administered in association with an antibiotic.

5. A method according to claim 1, wherein said transferrin is directly administered to epithelial cells and mocosae membranes.

6. A method according to claim 1, wherein said transferrin is in a liquid or lyophilized form.

7. A topical composition for inhibiting penetration of Gram positive bacteria selected from the group consisting of *Staphylococcus aureus, Streptococcus pyogenes* and mixtures thereof of into epithelial cells consisting of an anti-invasive and non-cytotoxic nor bactericidal amount of a transferrin selected from the group consisting of lactoferrin, ovotransferrin, serotransferrin and mixtures thereof, in association with a pharmaceutically acceptable carrier.

8. A topical composition according to claim 7, wherein said composition is in a liquid form and said transferrin is present at a concentration of up 2% by weight/volume.

9. A topical composition according to claim 7, wherein said transferrin is a lactoferrin in the apo or iron-saturated form.

10. A topical composition for inhibiting penetration of Gram positive bacteria selected from the group consisting of *Staphylococcus aureus, Streptococcus pyogenes* and mixtures thereof into epithelial cells consisting of an anti-invasive and non-cytotoxic nor bactericidal amount of a transferrin selected from the group consisting of lactoferrin, ovotransferrin, serotransferrin and mixtures thereof, in association with an antibiotic and a pharmaceutically acceptable carrier.

11. A topical composition according to claim 10, wherein said composition is in a liquid form and said transferrin is present at a concentration of up 2% by weight/volume.

12. A topical composition according to claim 10, wherein said transferrin is a lactoferrin in the apo or iron-saturated form.

* * * * *